(12) United States Patent
Mulligan (10) Patent No.: US 7,790,946 B2
(45) Date of Patent: Sep. 7, 2010

(54) SUBATMOSPHERIC PRESSURE WOUND THERAPY DRESSING

(75) Inventor: Sharon Mulligan, Bristol, RI (US)

(73) Assignee: Tyco Healthcare Group LP, Mansfield, MA (US)

( * ) Notice: Subject to any disclaimer, the term of this patent is extended or adjusted under 35 U.S.C. 154(b) by 269 days.

(21) Appl. No.: 11/825,480

(22) Filed: Jul. 6, 2007

(65) Prior Publication Data

US 2009/0012441 A1    Jan. 8, 2009

(51) Int. Cl.
*A61F 13/00* (2006.01)
*A61F 13/02* (2006.01)
*A61M 27/00* (2006.01)

(52) U.S. Cl. .............................. 602/57; 602/41; 602/42; 604/307; 604/543

(58) Field of Classification Search ................. 128/897, 128/898; 602/42, 43, 44, 45, 46, 47, 48, 602/49, 50, 51, 52, 53; 604/304, 305, 307, 604/543, 308, 313; 424/443–449
See application file for complete search history.

(56) References Cited

U.S. PATENT DOCUMENTS

| | | | |
|---|---|---|---|
| 1,626,493 A | | 4/1927 | Zimmerli et al. |
| 2,823,672 A | * | 2/1958 | Schladermundt et al. ...... 602/57 |
| 3,568,675 A | * | 3/1971 | Harvey ........................ 604/355 |
| 4,969,880 A | | 11/1990 | Zamierowski |
| 5,100,396 A | | 3/1992 | Zamierowski |
| 5,106,629 A | | 4/1992 | Cartmell et al. |
| 5,141,503 A | | 8/1992 | Sewell, Jr. |
| 5,176,663 A | | 1/1993 | Svedman et al. |
| 5,227,227 A | * | 7/1993 | Boulanger ................... 442/409 |
| 5,261,893 A | | 11/1993 | Zamierowski |
| 5,527,293 A | | 8/1996 | Gross |
| 5,636,643 A | * | 6/1997 | Argenta et al. .............. 128/897 |
| 5,645,081 A | | 7/1997 | Argenta et al. |

(Continued)

FOREIGN PATENT DOCUMENTS

EP    0 853 950 A1    7/1998

(Continued)

OTHER PUBLICATIONS

International Search Report, Application No. PCT/US/08/69291 dated Sep. 12, 2008.

(Continued)

*Primary Examiner*—Patricia M Bianco
*Assistant Examiner*—Ophelia Hawthorne
(74) *Attorney, Agent, or Firm*—Elizabeth A. O'Brien, Esq.

(57) ABSTRACT

A wound dressing apparatus for use in subatmospheric pressure therapy includes an outer member dimensioned for positioning relative to a wound bed and defining an internal reservoir, a port associated with the outer member and in communication with the internal reservoir for applying subatmospheric pressure to the internal reservoir to facilitate treatment of the wound bed and removal of fluid therefrom, an inner member at least partially positionable within the wound bed and confined within the outer member, and an adhesive agent in contact with a peripheral section of the outer member to facilitate attachment of the peripheral section to the periwound tissue. The adhesive agent is preferably substantially devoid of contact with the inner member. In one embodiment, a layer of adhesive material is disposed on the peripheral section of the outer member.

19 Claims, 6 Drawing Sheets

U.S. PATENT DOCUMENTS

| | | | |
|---|---|---|---|
| 5,678,564 A | 10/1997 | Lawrence et al. | |
| 5,701,917 A | 12/1997 | Khouri | |
| 5,759,570 A * | 6/1998 | Arnold | 424/443 |
| 5,866,642 A | 2/1999 | McVay et al. | |
| 5,911,222 A | 6/1999 | Lawrence et al. | |
| 6,071,267 A | 6/2000 | Zamierowski | |
| 6,117,111 A | 9/2000 | Fleischmann | |
| 6,135,116 A | 10/2000 | Vogel et al. | |
| 6,142,982 A | 11/2000 | Hunt et al. | |
| 6,174,306 B1 | 1/2001 | Fleischmann | |
| 6,261,276 B1 | 7/2001 | Reitsma | |
| 6,325,788 B1 | 12/2001 | McKay | |
| 6,345,623 B1 | 2/2002 | Heaton et al. | |
| 6,398,767 B1 | 6/2002 | Fleischmann | |
| 6,458,109 B1 | 10/2002 | Henley et al. | |
| 6,488,643 B1 | 12/2002 | Tumey et al. | |
| 6,520,982 B1 | 2/2003 | Boynton et al. | |
| 6,553,998 B2 | 4/2003 | Heaton et al. | |
| 6,557,704 B1 | 5/2003 | Randolph | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,752,794 B2 | 6/2004 | Lockwood et al. | |
| 6,755,807 B2 * | 6/2004 | Risk et al. | 604/319 |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 * | 2/2005 | Lockwood et al. | 604/313 |
| 6,855,860 B2 | 2/2005 | Ruszczak et al. | |
| 6,856,821 B2 | 2/2005 | Johnson | |
| 6,887,228 B2 | 5/2005 | McKay | |
| 6,936,037 B2 | 8/2005 | Bubb et al. | |
| 6,942,633 B2 | 9/2005 | Odland | |
| 6,942,634 B2 | 9/2005 | Odland | |
| 6,951,553 B2 | 10/2005 | Bubb et al. | |
| 6,979,324 B2 | 12/2005 | Bybordi et al. | |
| 6,994,702 B1 | 2/2006 | Johnson | |
| 7,004,915 B2 | 2/2006 | Boynton et al. | |
| 7,022,113 B2 | 4/2006 | Lockwood et al. | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,868 B1 | 10/2006 | Japuntich et al. | |
| 7,117,869 B1 | 10/2006 | Heaton et al. | |
| 7,125,391 B2 | 10/2006 | Joze et al. | |
| 7,128,735 B2 | 10/2006 | Weston | |
| 7,144,390 B1 | 12/2006 | Hannigan et al. | |
| 7,195,624 B2 | 3/2007 | Lockwood et al. | |
| 7,198,046 B1 | 4/2007 | Argenta et al. | |
| 7,214,202 B1 | 5/2007 | Vogel et al. | |
| 7,216,651 B2 | 5/2007 | Argenta et al. | |
| 7,361,184 B2 * | 4/2008 | Joshi | 606/213 |
| 2001/0031943 A1 | 10/2001 | Urie | |
| 2001/0043943 A1 | 11/2001 | Coffey | |
| 2002/0016577 A1 | 2/2002 | Ohmstede | |
| 2002/0143286 A1 | 10/2002 | Tumey | |
| 2002/0151836 A1 | 10/2002 | Burden | |
| 2003/0093041 A1 | 5/2003 | Risk, Jr. et al. | |
| 2003/0208149 A1 | 11/2003 | Coffey | |
| 2003/0212357 A1 | 11/2003 | Pace | |
| 2003/0212359 A1 | 11/2003 | Butler | |
| 2003/0219469 A1 | 11/2003 | Johnson et al. | |
| 2004/0006319 A1 | 1/2004 | Lina et al. | |
| 2004/0030304 A1 | 2/2004 | Hunt et al. | |
| 2004/0039391 A1 | 2/2004 | Argenta et al. | |
| 2004/0039415 A1 | 2/2004 | Zamierowski | |
| 2004/0064111 A1 | 4/2004 | Lockwood et al. | |
| 2004/0064132 A1 | 4/2004 | Boehringer et al. | |
| 2004/0073151 A1 | 4/2004 | Weston | |
| 2004/0093026 A1 | 5/2004 | Weidenhagen et al. | |
| 2004/0122434 A1 | 6/2004 | Argenta et al. | |
| 2004/0167482 A1 | 8/2004 | Watson | |
| 2004/0193218 A1 | 9/2004 | Butler | |
| 2004/0225208 A1 | 11/2004 | Johnson | |
| 2004/0241213 A1 | 12/2004 | Bray | |
| 2004/0243073 A1 | 12/2004 | Lockwood et al. | |
| 2004/0249353 A1 | 12/2004 | Risks, Jr. et al. | |
| 2004/0260230 A1 | 12/2004 | Randolph | |
| 2005/0010153 A1 | 1/2005 | Lockwood et al. | |
| 2005/0020955 A1 | 1/2005 | Sanders et al. | |
| 2005/0070835 A1 | 3/2005 | Joshi | |
| 2005/0070858 A1 | 3/2005 | Lockwood et al. | |
| 2005/0080372 A1 * | 4/2005 | Nielsen et al. | 602/42 |
| 2005/0085795 A1 | 4/2005 | Lockwood et al. | |
| 2005/0090787 A1 | 4/2005 | Risk, Jr. et al. | |
| 2005/0131327 A1 | 6/2005 | Lockwood et al. | |
| 2005/0137539 A1 | 6/2005 | Biggie et al. | |
| 2005/0147562 A1 | 7/2005 | Hunter et al. | |
| 2005/0177190 A1 | 8/2005 | Zamierowski | |
| 2005/0182445 A1 | 8/2005 | Zamierowski | |
| 2005/0222527 A1 | 10/2005 | Miller et al. | |
| 2005/0222544 A1 | 10/2005 | Weston | |
| 2005/0261642 A1 | 11/2005 | Weston | |
| 2005/0261643 A1 | 11/2005 | Bybordi et al. | |
| 2006/0015087 A1 | 1/2006 | Risk, Jr. et al. | |
| 2006/0025727 A1 | 2/2006 | Boehringer et al. | |
| 2006/0041247 A1 | 2/2006 | Petrosenko et al. | |
| 2006/0079852 A1 | 4/2006 | Bubb et al. | |
| 2006/0100586 A1 | 5/2006 | Karpowicz et al. | |
| 2006/0100594 A1 | 5/2006 | Adams et al. | |
| 2006/0116620 A1 | 6/2006 | Oyaski | |
| 2006/0129137 A1 | 6/2006 | Lockwood et al. | |
| 2006/0149170 A1 | 7/2006 | Boynton et al. | |
| 2006/0155369 A1 | 7/2006 | Edwin et al. | |
| 2006/0189910 A1 | 8/2006 | Johnson et al. | |
| 2006/0213527 A1 | 9/2006 | Argenta et al. | |
| 2007/0005028 A1 | 1/2007 | Risk, Jr. et al. | |
| 2007/0014837 A1 | 1/2007 | Johnson et al. | |
| 2007/0021697 A1 | 1/2007 | Ginther et al. | |
| 2007/0021698 A1 | 1/2007 | Fleischmann | |
| 2007/0027414 A1 | 2/2007 | Hoffman et al. | |
| 2007/0031463 A1 * | 2/2007 | Fotinos et al. | 424/405 |
| 2007/0032754 A1 | 2/2007 | Walsh | |
| 2007/0032755 A1 | 2/2007 | Walsh | |
| 2007/0032762 A1 | 2/2007 | Vogel | |
| 2007/0032778 A1 | 2/2007 | Heaton et al. | |
| 2007/0038172 A1 | 2/2007 | Zamierowski | |
| 2007/0055209 A1 | 3/2007 | Patel et al. | |
| 2007/0066946 A1 * | 3/2007 | Haggstrom et al. | 604/313 |
| 2007/0073200 A1 | 3/2007 | Hannigan et al. | |
| 2007/0078366 A1 | 4/2007 | Haggstrom et al. | |
| 2007/0225663 A1 * | 9/2007 | Watt et al. | 604/313 |

FOREIGN PATENT DOCUMENTS

| | | |
|---|---|---|
| EP | 1 088 569 A2 | 4/2001 |
| EP | 1 219 311 A2 | 7/2002 |
| GB | 2 307 180 A | 5/1997 |
| GB | 2 329 127 A | 3/1999 |
| GB | 2 336 546 A | 10/1999 |
| GB | 2 344 531 A | 6/2000 |
| WO | WO 93/09727 | 5/1993 |
| WO | WO 94/20041 | 9/1994 |
| WO | WO 96/05873 | 2/1996 |
| WO | WO 00/21586 | 4/2000 |
| WO | WO 03/005943 A2 | 1/2003 |
| WO | WO 03/030966 A1 | 4/2003 |
| WO | WO 03/045492 A1 | 6/2003 |
| WO | WO 03/057070 A2 | 7/2003 |
| WO | WO 03/057071 A2 | 7/2003 |

| | | |
|---|---|---|
| WO | WO 03/057307 A1 | 7/2003 |
| WO | WO 03/086232 A2 | 10/2003 |
| WO | WO 03/092620 A2 | 11/2003 |
| WO | WO 03/101508 A2 | 12/2003 |
| WO | WO 2004/018020 A1 | 3/2004 |
| WO | WO 2005/009488 A2 | 2/2005 |

OTHER PUBLICATIONS

US 7,186,244, 03/2007, Hunt et al. (withdrawn)

* cited by examiner

SUBATMOSPHERIC PRESSURE WOUND THERAPY DRESSING

BACKGROUND

1. Technical Field

The present disclosure relates to an apparatus for treating an open wound, and, more specifically, relates to a wound dressing for use in a subatmospheric pressure wound therapy procedure.

2. Description of Related Art

Wound closure involves the migration of epithelial and subcutaneous tissue adjacent the wound towards the center of the wound until the wound closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Wound dressings have been used in the medical industry to protect and/or facilitate healing of open wounds. One popular technique has been to use negative pressure therapy, which is also known as suction or vacuum therapy. A variety of negative pressure devices have been developed to allow excess wound fluids, i.e., exudates, to be removed while at the same time isolating the wound to protect the wound and, consequently, reduce recovery time. Various wound dressings have been employed to promote the healing of open wounds.

SUMMARY

Accordingly, the present disclosure is directed to further improvements in subatmospheric pressure wound therapy. In one preferred embodiment, a wound dressing apparatus includes an outer member dimensioned for positioning relative to a wound bed and defining an internal reservoir, a port associated with the outer member and in communication with the internal reservoir for applying subatmospheric pressure to the internal reservoir to facilitate treatment of the wound bed and removal of fluid therefrom, an inner member at least partially positionable within the wound bed and confined within the outer member, and an adhesive agent in contact with a peripheral section of the outer member to facilitate attachment of the peripheral section to the periwound tissue. The adhesive agent is preferably substantially devoid of contact with the inner member such that the integrity of the inner member is not affected or degraded, due to its otherwise contact with the inner member. In one embodiment, a layer of adhesive material is disposed on the peripheral section of the outer member.

A release member may be mounted to the layer of the adhesive material in at least partial superposed relation with the outer member. The release member is removable to expose the adhesive material. The layer of the adhesive material may be disposed on a major portion of one surface of the outer member. In another embodiment, the release member may define a plurality of release sections. The release sections may be selectively separable to expose a predetermined area of the layer of the adhesive material for attachment to the periwound tissue.

A supplemental member may be positioned over the inner member, to prevent contact of the adhesive layer with the inner member. The supplemental member may include a layer of gauze.

The adhesive agent may be a liquid agent applicable to the peripheral section of the outer member or applicable to the periwound tissue prior to attachment thereof to the periwound tissue. The adhesive agent may be thermally activated, adapted to be activated through application of ultraviolet energy, or adapted to be activated upon exposure to an exothermic catalyst.

In another embodiment, a pad member has the adhesive agent on one surface thereof. The pad member is dimensioned to be positioned about the peripheral section of the outer member to at least partially overlap and adhere to each of the peripheral section and the periwound tissue to thereby secure the outer member to the periwound tissue.

The inner member may include a material selected from the group consisting of foams, beads, nonwoven composite fabrics, hydrogels, cellulosic fabrics, super absorbent polymers, and combinations thereof. The inner member further may include at least one of a medicament, an anti-infective agent, an antimicrobial, polyhexamethylene biguanide (hereinafter, "PHMB"), antibiotics, analgesics, healing factors, vitamins, growth factors, debridement agents and nutrients.

A subatmospheric pressure source may be in fluid communication with the port. The subatmospheric pressure source supplies subatmospheric pressure to the internal reservoir.

BRIEF DESCRIPTION OF THE DRAWINGS

Various embodiments of the subject wound dressing are described herein with reference to the drawings wherein.

DESCRIPTION OF THE PREFERRED EMBODIMENTS

The composite wound dressing of the present disclosure promotes healing of a wound via the use of a subatmospheric pressure reservoir. The subatmospheric pressure reservoir subjects the wound to subatmospheric pressure or a vacuum to effectively draw wound fluid, including liquid, exudates from the wound bed with continuous, or non-continuous, application of a subatmospheric pressure source or pump. Hence, subatmospheric pressure can be applied once, or in varying intervals, depending on the nature and severity of the wound until the composite wound dressing is saturated with exudate or the wound is healed. If the wound dressing is saturated with exudate and the wound is not healed, the composite wound dressing can be replaced and the process of applying subatmospheric pressure can be repeated.

Figure 1:
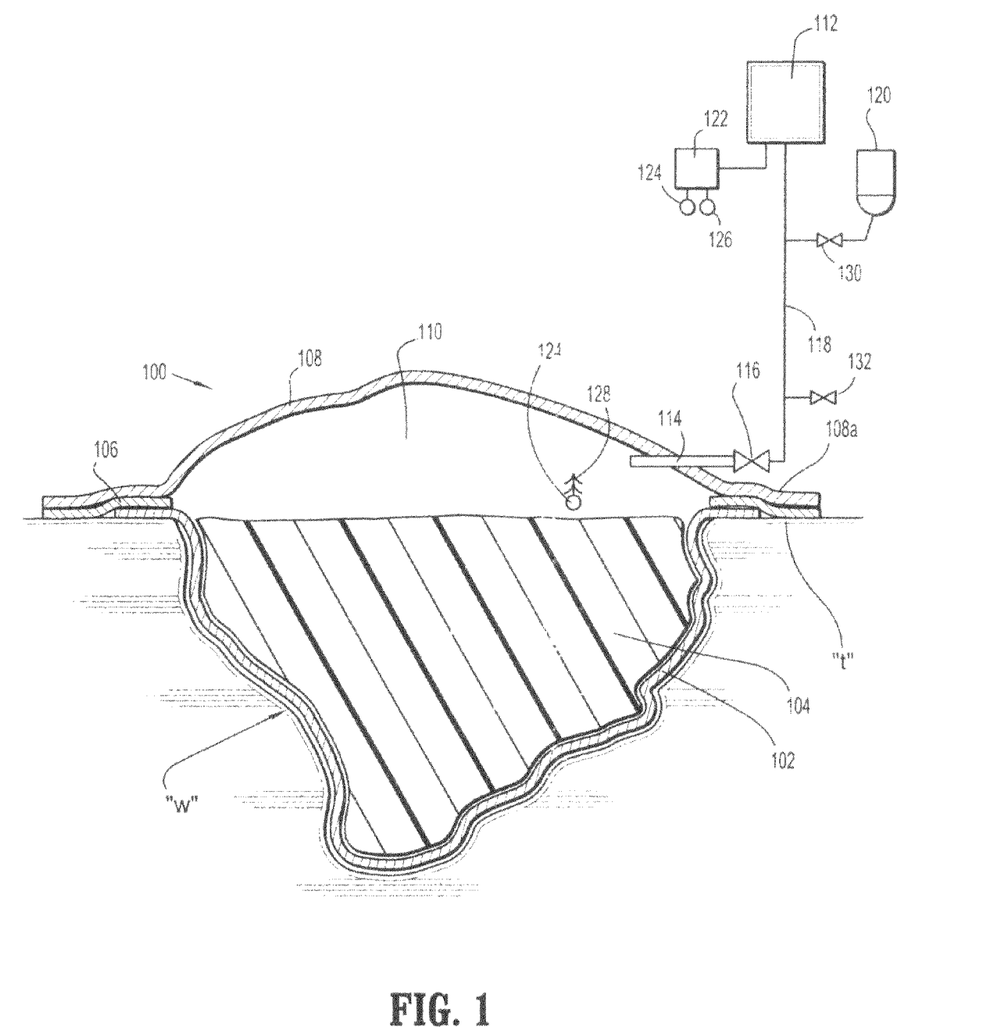
FIG. 1 is a side cross-sectional view of the wound dressing apparatus in accordance with the principles of the present disclosure positioned about a wound bed illustrating the outer member, inner member, adhesive member and the wound liner.
Figure 2:
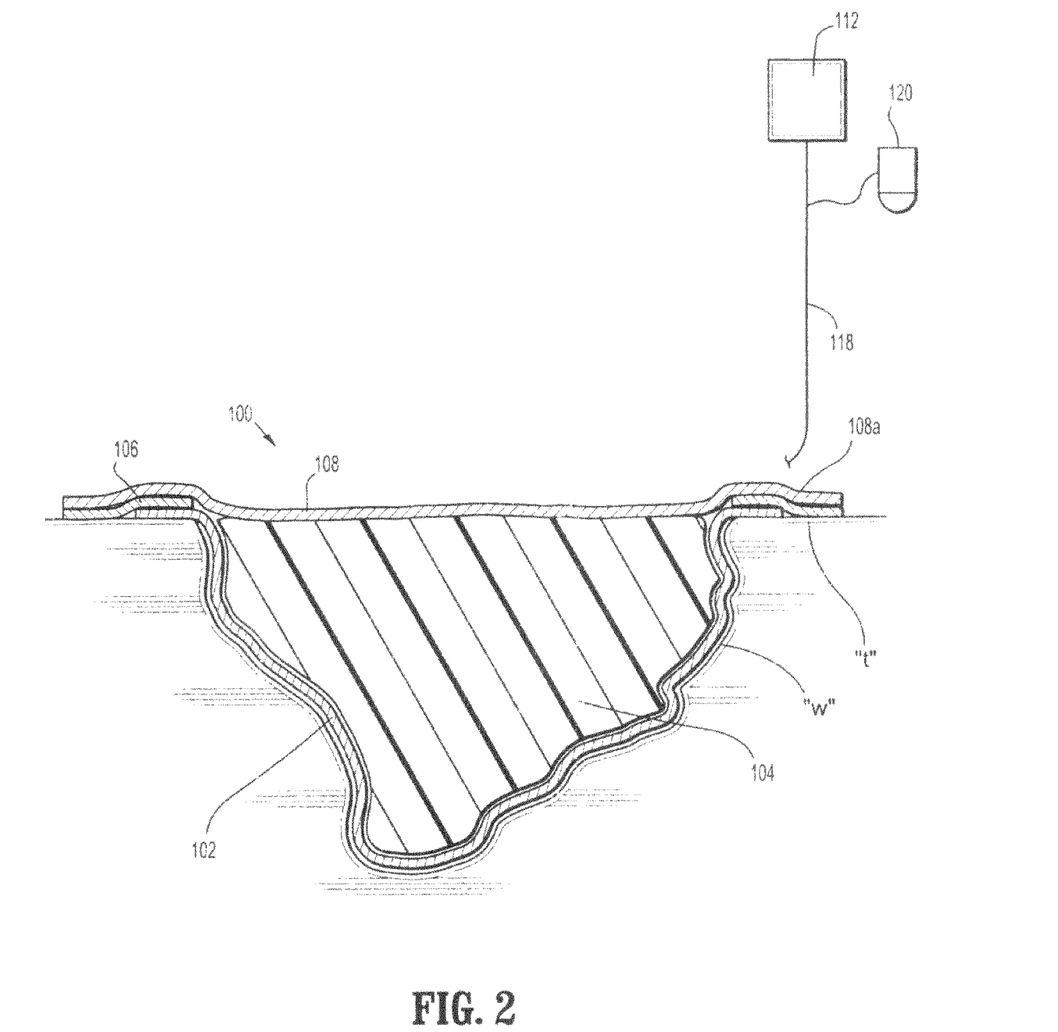
FIG. 2 is a view similar to the view of FIG. 1 illustrating the wound dressing subjected to subatmospheric pressure.

Referring now to FIGS. 1-2, the composite wound dressing apparatus 100 in accordance with a preferred embodiment of the present disclosure is illustrated in the form of an article with multiple layers arranged in juxtaposed or superposed relation. The multiple layers include, but, are not limited to a wound liner 102, an inner member 104 an adhesive agent or member 106, and an outer member 108 which includes and/or defines the internal subatmospheric pressure reservoir 110.

The wound liner 102 is in direct contact with the wound bed "w". The wound liner 102 is typically porous allowing passage of subatmospheric pressure to the wound bed. In one preferred embodiment, the base layer includes a "non-adherent" material. "Non-adherent" as used herein refers to a material that does not adhere to tissues in and around the wound bed. "Porous" as used herein refers to a material which contains numerous small perforations or pores which allow wound fluids to pass through the material to the dressing layers above. The passage of wound fluid through the porous material may be unidirectional such that wound exudate does not flow back to the wound bed. This direction flow feature could be in the form of directional apertures imparted into the material layer, a lamination of materials of different absorption to the wound liner 102 or specific material selection that encourages directional flow. Exemplary materials used as the wound liner 102 include a contact layer sold under the trademark XEROFLOW® by Kendall Corp., a division of TycoHealthcare. In the alternative, wound dressing apparatus 100 may be devoid of the wound liner 102.

In addition, agents such as hydrogels, adhesives and medicaments could be bonded or coated to the wound liner 102 to reduce bioburden in the wound, promote healing and reduce pain associated with dressing changes or removal. Medicaments include, for example, antimicrobial agents, growth factors, antibiotics, analgesics, debridement agents and the like. Furthermore, when an analgesic is used, the analgesic could include a mechanism that would allow the release of that agent prior to dressing removal or change. Exemplary triggers of a release mechanism could be temperature change, moisture, ph, pressure and the like.

Inner member 104 may serve as an absorbent/packing layer. In this capacity, inner member 104 is intended to absorb and capture wound fluid and exudates. Exemplary absorbent materials include foams, nonwoven composite fabrics, fibers, hydrogels, cellulosic fabrics, alginates, super absorbent polymers, hydrophilic and hydrophobic beads, and combinations thereof. Typically, the inner member 104 can absorb up to about 100 cubic centimeters (cc) or more of wound fluid. The absorbent material may include the antimicrobial dressing sold under the trademark KERLIX® by Kendall Corp., a division of TycoHealthcare. In one embodiment, the inner member 104 could be preformed or shaped to conform to varying shapes of the wound bed. Those skilled in the art will recognize that the inner member 104 can be formed in any suitable shape. The inner member 104 may include multiple layers.

Additionally, the inner member 104 could be treated with medicaments. Medicaments include, for example, an anti-infective agent such as an antiseptic or other suitable antimicrobial or combination of antimicrobials, polyhexamethylene biguanide (hereinafter, "PHMB"), antibiotics, analgesics, healing factors such as vitamins, growth factors, nutrients and the like, as well as a flushing agent such as isotonic saline solution.

With continued reference to FIGS. 1-2, the adhesive member 106 at least encompasses the perimeter of the wound dressing 100 to surround the wound bed to provide a seal around the perimeter of the wound bed "w". For instance, the sealing mechanism may be any adhesive bonded to a layer that surrounds the wound bed "w" or an adhesive applied directly to the skin. The adhesive must provide acceptable adhesion to the periwound tissue "t" surrounding the wound bed "w" skin, e.g., the periwound area, and be acceptable for use on skin without contact deterioration (for example, the adhesive should preferably be non-irritating and non-sensitizing.) Typical adhesives can include acrylics, silicone, urethanes, hydrogels, rubber-based hydrogels and the like. The adhesive may be semi-permeable to permit the contacted skin to transmit moisture or may be impermeable. Additionally, the adhesive could be activated or de-activated by an external stimulus such as heat, light or a given fluid solution or chemical reaction. Adhesives include, for example, the dressing sold under the trademark ULTEC® Hydrocolloid or hydrogel sold under the trademarks of Curagel® or Aqua Flo® dressing by Kendall Corp., a division of TycoHealthcare.

In one embodiment, the adhesive member 106 is a layer of adhesive material, i.e., incorporated within or a component of the outer member 108. Releasable contact liners may be incorporated within the outer member 108 to protect the adhesive member 106 prior to use as will be discussed. The adhesive member 106 may also be in the form of an entire layer proximal to the inner member 104, or, may be annular or "donut shaped" as shown. Preferably, the adhesive member 106 is not bonded to the inner member 104. In one embodiment, the adhesive member 106 is a component of the periphery of the outer member 108. The adhesive member 106 is secured to the outskirts of the wound liner 102 and at least bonded to the periwound tissue "t" to be in overlapping relation with the tissue "t". Alternatively, the adhesive member 106 may be positioned on the peripheral portion of the outer member 108 and secured to the tissue "t" about the wound bed "w", and not bonded to the wound liner 102. As a further alternative, the adhesive member 106 may be a liquid substance applied to the peripheral portion of the outer member 108 or the periwound tissue "t" prior to application of the wound dressing apparatus 100. Preferably, the adhesive member 106 is substantially devoid of contact with the inner member 104. With this relation, the adhesive member 106 will not affect the integrity of the inner member 104 nor come into contact with the healing tissue within the wound bed "w".

The outer member 108 typically seals the top of the wound dressing 100 and helps maintain the appropriate subatmospheric pressure level within the wound dressing 100. In one preferred embodiment, the outer member 108 includes the flexible transparent dressing manufactured under the trademark POLYSKIN® II by Kendall Corp., a division of TycoHealthcare. POLYSKIN® II is a transparent, semi-permeable material which permits moisture and oxygen exchange with the wound site, and provides a barrier to microbes and fluid containment. In another approach, the outer member 110 may be impermeable. As a further alternative, the outer member 108 may include a resilient, e.g., elastomeric, material in the shape, e.g., of a dome.

The outer member 108 defines a sealed or enclosed subatmospheric pressure reservoir 110. The subatmospheric pressure reservoir 110 is preferably maintained at an appropriate subatmospheric pressure level for a predetermined period of time sufficient to initiate or complete healing of the wound bed "w", i.e., to draw wound fluid and exudate away from the wound bed "w" while subjecting the wound to subatmospheric pressure. The subatmospheric pressure may be reapplied as needed to maintain a therapeutic effect. The subatmospheric pressure may be continuous or intermittent as desired.

As best seen in FIG. 1, the subatmospheric pressure reservoir 110 is defined within the dome of the outer member 108. As shown in FIG. 2, once subatmospheric pressure is applied via the subatmospheric pressure source 112, the dome of the outer member 108 is drawn downwardly toward the inner member 104 with the subatmospheric pressure or subatmospheric reservoir 110 created beneath the outer member 108. Typically, the outer member 108 includes a subatmospheric pressure port or connector 114 in fluid communication with the subatmospheric pressure reservoir 110. Preferably, the subatmospheric pressure port 114 includes a one-way valve (shown schematically as reference numeral 116) which provides unidirectional flow of suction and may provide a means for allowing connection of the composite wound dressing 100 to the subatmospheric pressure source 112. The one way valve 116 may be incorporated within the subatmospheric pressure port 114 or, alternatively, be "in line" with the subatmospheric pressure source 112. A flexible tubing 118 is connected to the subatmospheric pressure port 114 and the subatmospheric pressure source 112. The tubing 118 provides suction to the wound from the subatmospheric pressure source 112 and enables the wound fluid or exudates to be transferred from the wound dressing 100. The tubing 118 may be fabricated from PVC, silicone based material or other flexible materials (polymers). The tubing 118 may optionally include a connection to a collection canister 120 for wound drainage and debris. Hence, the subatmospheric pressure source 112 can draw wound fluid through the composite wound dressing 100 and tubing 118 into the canister 120. In a preferred embodiment of the present disclosure, the canister 120 is portable so that the patient will have the freedom to move about rather than being confined to a fixed location. The canister 120 may also house an absorbent material to absorb wound fluid and exudate.

The subatmospheric pressure source 112 may apply subatmospheric pressure to the wound by means such as a manual pump as disclosed in commonly assigned U.S. Pat. No. 5,549,584 to Gross, the entire contents of which are hereby incorporated herein by reference. In the alternative, the subatmospheric pressure source 112 may include an automated pump. Typically, the subatmospheric pressure level is applied to achieve a range between about 20 mmHg to about 500 mmHg, more preferably, about 40 mmHg and about 125 mmHg. The automated pump may be a wall suction apparatus such as those available in an acute or sub-acute care facility. The automated pump may be in the form of a portable pump. The portable pump may include a small or miniature pump that maintains or draws adequate and therapeutic subatmospheric pressure levels. In a preferred embodiment, the pump is a portable, lightweight, battery operated, suction pump which attaches to the distal end of the tubing. Typically, the subatmospheric pressure source 112 has regulation means 122 to apply the optimal subatmospheric pressure for healing the wound. The regulation means 122 may include one or more pressure sensors 124, 126. One pressure sensor 124 may be utilized to detect the pressure within the subatmospheric reservoir 110, and with the appropriate circuitry or logic associated with the regulations means 122, may adjust (e.g., increase or decrease), delay, halt, and/or commence the operation of the subatmospheric pressure source 112 to achieve a subatmospheric pressure objective adjacent the wound. The pressure sensor 124 may be remote from the wound and in fluid communication with the subatmospheric reservoir 110 through the tubing 118, or alternatively, may be positioned directly within the subatmospheric reservoir 110 and/or the wound dressing 100 and in electrical communication with the regulation means 122 through wiring or conduit extending through the tubing 118. It is further envisioned that the pressure sensor 124 may be capable of sending remote, e.g., wireless signals, from the wound site to the regulation means 122 through a transmitter 128 to control operation of the subatmospheric pressure source 112.

The pressure sensor 126 is envisioned to detect a change in pressure, e.g., an increase in negative pressure indicating that the canister 120 is full or near a full condition. In this embodiment, a filter 130 is disposed between the canister 120 and the subatmospheric pressure source 112. Once the canister 120 becomes full and the exudates communicates with the filter 130, the filter 130 becomes clogged or blocked and the subatmospheric pressure is substantially increased as detected by the pressure sensor 126. As a result, the subatmospheric pressure source 112 is switched to an off condition to permit subsequent emptying or disposal of the canister 120.

Tubing connector 114, one-way valve 116 or tubing 118 may incorporate vent (schematically identified as numeral 132) to permit the clinician to manually vent to the atmosphere when a clog is connected, or to clear the lines of fluid. Vent 132 may be a valve which opens and closes or a perforated filter which may control leak rate so that the exudates may be able to be deposited into canister 120.

Furthermore, the subatmospheric pressure source 112 would preferably contain a mechanism to detect a leak in the system if the optimal subatmospheric pressure is not achieved. Preferably, the subatmospheric pressure source 112 would also contain an indicator (not shown) to indicate when the optimal subatmospheric pressure is achieved. In the alternative, a hand pump in the form of a squeeze bulb or a foot pump may serve as the subatmospheric pressure source 112.

Preferably, a pump is used as the subatmospheric pressure source 112. Typical pumps include diaphragm or voice coil activated styles that can deliver variable subatmospheric pressure up to 18 liters/minute.

Figure 3:
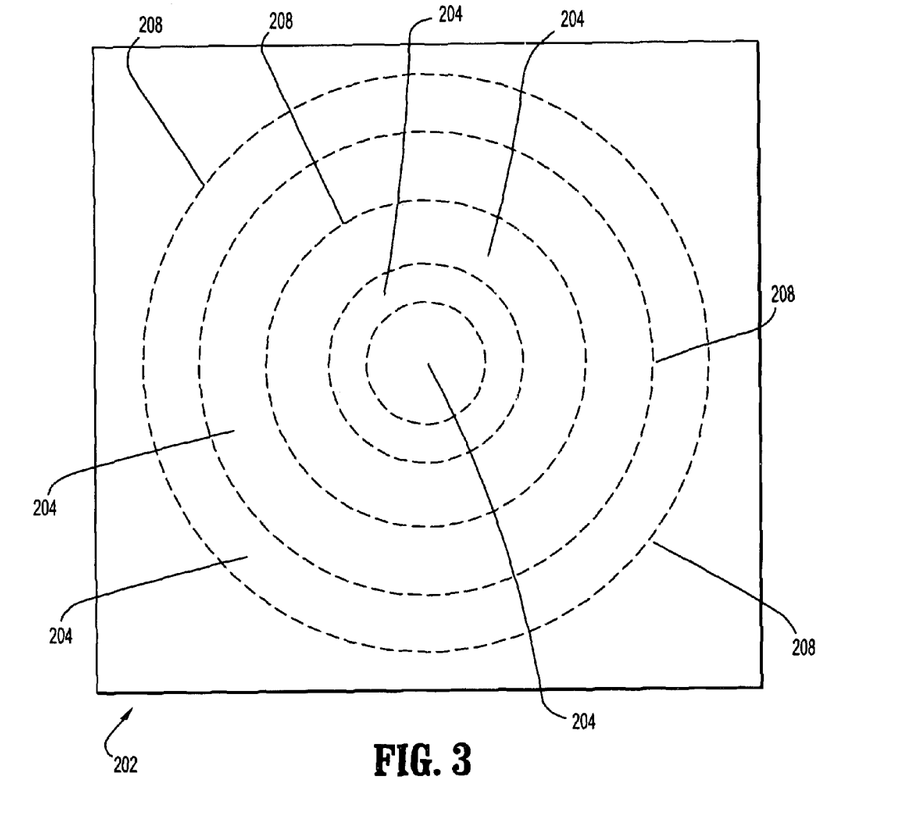
FIG. 3 is a plan view of an outer member in accordance with an alternate embodiment of the wound dressing.
Figure 4:
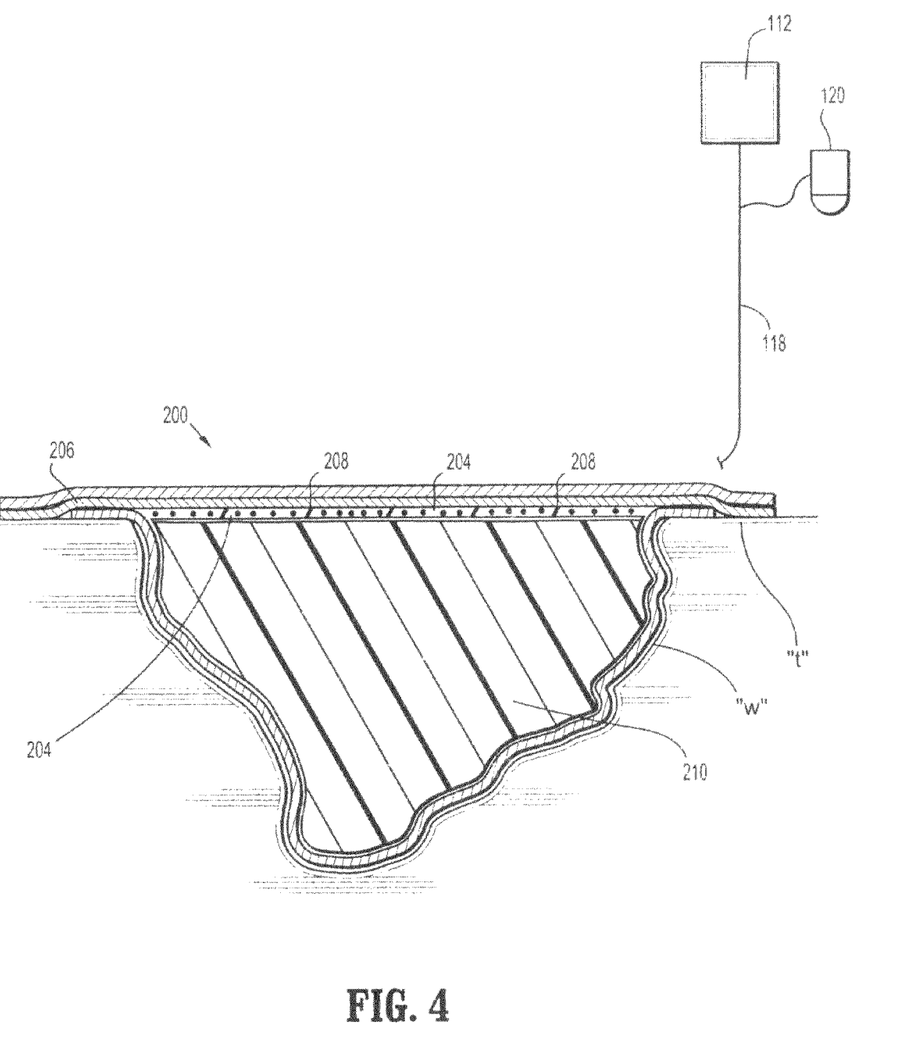
FIG. 4 is a side cross-sectioned similar to the view of FIG. 2 illustrating the wound dressing of FIG. 3 positioned about the wound bed.

FIGS. 3-4 illustrate an alternate embodiment of the wound dressing apparatus 200 of the present disclosure. In accordance with this embodiment, outer member 202 includes a plurality of releasable liner sections 204 which cover the adhesive agent or member 206 disposed on the lower surface of the outer member 202. The releasable liner sections 204 are independently separable from the outer member 202 about the perforated lines or score lines 208 to selectively expose the adhesive member 206 to generally correspond to the size of the wound bed. In one embodiment, the outer member 202 includes a plurality of concentric annular or circular releasable liner sections 204. Thus, the clinician may remove the outer liner sections 204 as desired to expose the adhesive member 206 for securement of the outer member 202 to the periwound tissue "t". The inner releasable liner sections 204 may be retained on the outer member 202 as desired to ensure that the adhesive member 206 will not come into contact with the inner member 210 as shown in FIG. 4.

Figure 5:
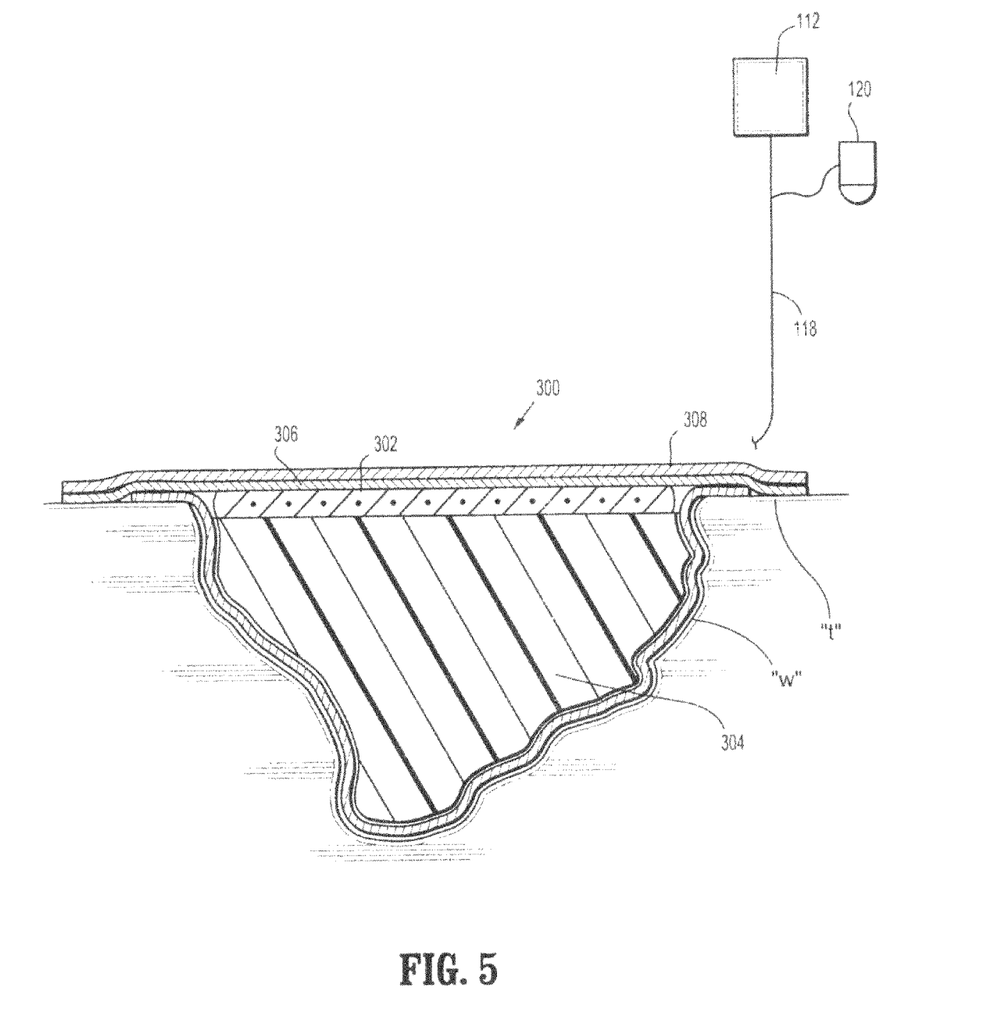
FIG. 5 is a side cross-sectional view similar to the view of FIG. 2 illustrating another embodiment of the wound dressing apparatus.

FIG. 5 illustrates an alternate embodiment of the wound dressing apparatus 300. Wound dressing apparatus 300 may incorporate a supplemental member 302 positionable between the inner member 304 and the adhesive member 306 which may or may not be a component of the outer member 308. The supplemental member 302, thus, is in contact with the adhesive member 306 thereby preventing exposure of the inner member 304 to the adhesive member 306. In one embodiment, the supplemental member 302 may be a gauze material such as the aforementioned KERLIX® and the inner member 304 may include a foam material.

Figure 6:
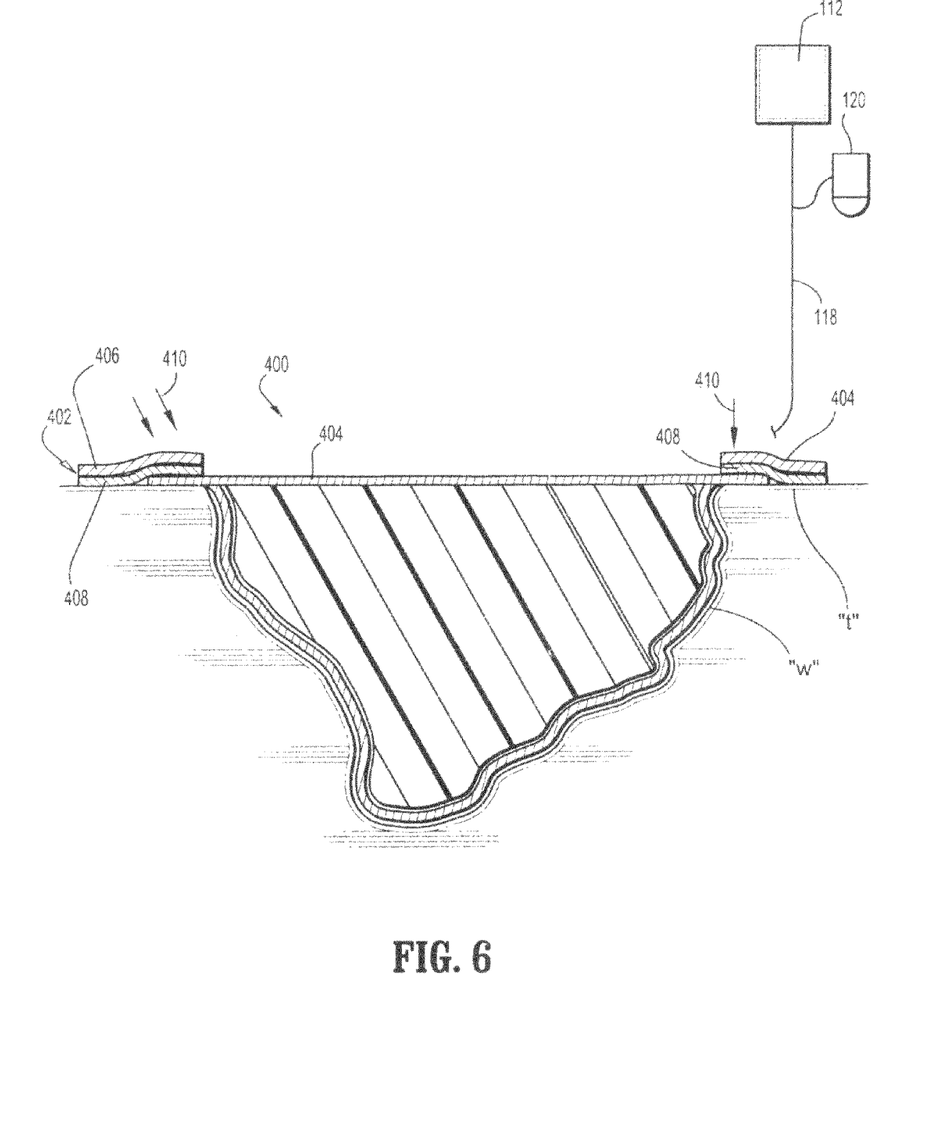
FIG. 6 is a side cross-sectioned view similar to the view of FIG. 2 illustrating another embodiment of the wound dressing apparatus.

FIG. 6 illustrates an alternative embodiment of the wound dressing apparatus 400. In accordance with this embodiment, the adhesive member 402 is an annular or ring like member which is positionable onto the upper surface of the outer member 404. The adhesive member 402 may include a base member 406 having a layer of adhesive 408 disposed on the base member 406. A releasable liner may be positioned on the adhesive member 402 to protect the adhesive during transport. In use, the releasable liner may be removed to expose the adhesive member 402. Thereafter, the adhesive member 402 is mounted to the outer surface of the outer member 404 and arranged to overlap the outer member 404 and the periwound tissue "t" thus securing the outer member 404 to the patient. In one embodiment, the adhesive member 402, i.e., the layer of adhesive material 408, is thermally activated with the application of a thermal energy source as shown schematically by arrows 410. In one aspect, the adhesive member 402 is activated by ultraviolet light. Alternatively, the adhesive member 402 is adapted to be activated upon exposure to an exothermic catalyst.

It is further contemplated that the wound dressing apparatus may incorporate external means or applications to stimulate tissue growth and/or healing. For example, an ultrasonic transducer may be incorporated into the wound dressing apparatus to impart mechanical energy for the treatment of the tissue such as, for instance, directing thermal or vibratory energy on the wound area to stimulate healing and/or further encouraging exudates removal by subatmospheric pressure and/or introducing various drugs into the human body through the skin. Other sensor types are also contemplated for incorporation into the wound dressing apparatus including oxygen, chemical, microbial and/or temperature sensors. The detection of oxygen adjacent the wound area would assist the clinician in determining the status of wound healing. The presence of an elevated temperature may be indicative of an infection.

While the disclosure has been illustrated and described, it is not intended to be limited to the details shown, since various modifications and substitutions can be made without departing in any way from the spirit of the present disclosure. Accordingly, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A wound dressing apparatus for use in subatmospheric pressure therapy, which comprises:
   an outer member dimensioned for positioning relative to a wound bed to substantially enclose the wound bed, the outer member defining an internal reservoir;
   a port associated with the outer member and in communication with the reservoir for applying subatmospheric pressure to the reservoir to facilitate treatment of the wound bed and removal of fluid therefrom;
   an inner member at least partially positionable within the wound bed and confined within the outer member;
   a layer of an adhesive agent disposed on the outer member to facilitate attachment thereof relative to the wound bed; and
   a release member mounted to the layer of the adhesive agent in at least partial superimposed relation with the outer member, the release member defining a plurality of concentric release sections extending from a central release section substantially encompassing a centermost segment of the outer member, each release section being selectively separable to expose a predetermined area of the layer of the adhesive agent.

2. The wound dressing according to claim 1 wherein the layer of the adhesive agent is thermally activated.

3. The wound dressing according to claim 2 wherein the layer of the adhesive agent is adapted to be activated through application of ultraviolet energy.

4. The wound dressing according to claim 2 wherein the layer of the adhesive agent is adapted to be activated upon exposure to an exothermic catalyst.

5. The wound dressing according to claim 1 further including a supplemental member positionable over the inner member.

6. The wound dressing according to claim 5 wherein the supplemental member includes a layer of gauze.

7. The wound dressing apparatus according to claim 1 wherein the inner member comprises a material selected from the group consisting of foams, beads, nonwoven composite fabrics, hydrogels, cellulosic fabrics, super absorbent polymers, and combinations thereof.

8. The wound dressing apparatus according to claim 7 wherein the inner member includes at least one of a medicament, an anti-infective agent, an antimicrobial, polyhexamethylene biguanide (hereinafter, "PHMB"), antibiotics, analgesics, healing factors, vitamins, growth factors, debridement agents and nutrients.

9. The wound dressing apparatus according to claim 1 wherein the layer of the adhesive agent is disposed on the centermost segment of the outer member and extends outwardly toward a peripheral segment of the outer member.

10. The wound dressing apparatus according to claim 9 wherein the layer of adhesive is disposed on substantially an entire surface of the outer member.

11. The wound dressing apparatus according to claim 1 further including a subatmospheric pressure source in fluid communication with the port, the subatmospheric pressure source supplying subatmospheric pressure to the reservoir.

12. The wound dressing apparatus according to claim 1 wherein the release sections of the release member are independently separable about perforated lines to generally correspond to the size of the wound bed.

13. The wound dressing apparatus according to claim 1 wherein the concentric release sections of the release member are substantially annular sections and the central release section of the release member is a substantially circular section.

14. The wound dressing apparatus according to claim 1 wherein the outer member defines a peripheral segment, the layer of the adhesive agent being disposed on the peripheral segment for attaching to periwound tissue surrounding the wound bed.

15. A wound dressing apparatus for use in subatmospheric pressure therapy, which comprises:
   an outer member dimensioned for positioning relative to a wound bed to substantially enclose the wound bed, the outer member defining an internal reservoir over the wound bed;
   a port associated with the outer member and in communication with the reservoir for applying subatmospheric pressure to the reservoir to facilitate treatment of the wound bed and removal of fluid therefrom;
   an inner member at least partially positionable within the wound bed and confined within the outer member, the inner member adapted for capturing wound exudate;
   a layer of adhesive agent disposed on one surface of the outer member to facilitate attachment relative to the wound bed;

a supplemental member positionable over the inner member beneath the outer member to substantially prevent contact of the adhesive agent with the inner member;

a subatmospheric pressure source in fluid communication with the port, the subatmospheric pressure source supplying subatmospheric pressure to the reservoir; and a release member mounted to the layer of the adhesive agent in at least partial superimposed relation with the outer member, the release member defining a plurality of concentric release sections extending from a central release section substantially encompassing a centermost segment of the outer member, each release section being selectively separable to expose a predetermined area of the layer of the adhesive agent.

16. The wound dressing apparatus according to claim 15 wherein the release sections of the release member are independently separable about perforated lines to generally correspond to the size of the wound bed.

17. The wound dressing apparatus according to claim 15 wherein the layer of the adhesive agent is disposed at least adjacent the centermost segment of the outer member and extends outwardly toward a peripheral segment of the outer member.

18. A wound dressing apparatus for use in subatmospheric pressure therapy, which comprises:

an outer member dimensioned for positioning relative to a wound bed, and having an adhesive surface for attachment relative to periwound tissue surrounding the wound bed;

a port for applying subatmospheric pressure beneath the outer member to facilitate treatment of the wound bed;

an inner member at least partially positionable within the wound bed and dimensioned and adapted to one of collect or transfer fluids from the wound bed; and a release member mounted to the adhesive surface of the outer member, the release member defining a central release section in superposed relation with the centermost segment of the outer member and at least one outer release section concentrically arranged with respect to the central release section, each release section being selectively separable to permit a clinician to expose a predetermined area of the adhesive surface to generally correspond to the size of the wound bed whereby the exposed predetermined area of the adhesive surface may be secured at least to the periwound tissue surrounding the wound bed.

19. The wound dressing apparatus according to claim 18 including plurality of outer release sections concentrically arranged about the central release section.

* * * * *